United States Patent [19]

Nanba

[11] Patent Number: 4,501,497

[45] Date of Patent: Feb. 26, 1985

[54] CELL FOR MEASUREMENT

[75] Inventor: Yuzaburo Nanba, Saitama, Japan

[73] Assignee: Eisai Co., Ltd., Tokyo, Japan

[21] Appl. No.: 406,626

[22] Filed: Aug. 9, 1982

[30] Foreign Application Priority Data

Aug. 28, 1981 [JP] Japan .................................. 56-135245
Aug. 28, 1981 [JP] Japan .................................. 56-135246

[51] Int. Cl.³ ............................................. G01N 1/10
[52] U.S. Cl. ..................................... 356/246; 356/440
[58] Field of Search ................. 356/246, 440; 250/576

[56] References Cited

U.S. PATENT DOCUMENTS 3,097,928 7/1963 Staunton .......................... 356/246 X
3,225,601 12/1965 Shrewsbury ..................... 356/246 X
3,419,722 12/1968 Meikle .................................. 250/576
3,999,948 12/1976 Deindoerfer et al. ........... 356/246 X

FOREIGN PATENT DOCUMENTS 2220118 11/1973 Fed. Rep. of Germany ...... 356/246

Primary Examiner—Davis L. Willis
Assistant Examiner—Matthew W. Koren
Attorney, Agent, or Firm—Flynn, Thiel, Boutell & Tanis

[57] ABSTRACT

A cell, into which liquid sample to be measured is injected, is provided with a sample inlet and a sample receiving portion. In the sample receiving portion, a suction tube for discharging liquid is inserted to the bottom of the cell, an injection tube for cleaning liquid is provided in provity of the sample inlet, and the suction tube for discharging is connected to a suction pump through an electromagnetic valve, the injection tube being connected to a constant volume pump for injecting cleaning liquid.

The discharge of the sample by the suction pump, the injection of the cleaning liquid by the constant volume pump and the discharge of cleaning liquid by the suction pump are controlled by a sequential timer.

6 Claims, 5 Drawing Figures

CELL FOR MEASUREMENT

BACKGROUND OF THE INVENTION

The present invention relates to a cell for the optical measurement for measuring exactly, continuously and also effectively a sample of the minimum quantity required.

Generally, the absorbance of a liquid sample such as antibody, antigen, blood coagulation, blood serum, reaction liquid and others is measured using a device such as shown in FIG. 1. A liquid sample (2) is received by a cell of transparent glass for optical measurement.

A ray (4) having the wave length for example, of 300-500 nm is radiated from a light source (3) on one side of the cell to the sample through a slit plate (5). The absorbance of the ray (4) due to the sample (2) is detected by a detector (6) such as a photo tube on the other side of the cell.

Conventionally, in the optical measurement device such as this, so called standard cell (1) generally used has a shape of a square prism with an optical path length (L) of 10 mm as shown in FIG. (1). The sample receiving portion of the standard cell (1) is too large for optical measurement of the liquid sample (2) of anti body and others so that too much sample is required and a dense sample has to be diluted for measurement since it is hard to pass the ray of light therethrough.

Therefore, a cell of which sample receiving volume is reduced and the optical path length is shortened as shown in FIG. 2 is normally used. The cell shown in FIG. 2 has a shape of square prism like that of the standard cell (1) in FIG. (1), having an inner optical path length (L), for example, of 2-0.5 mm, this narrow portion being for receiving the sample. In this case, the defect as mentioned above is obviated.

However, simple narrowing of sample receiving portion makes the discharge of the sample once received and the cleaning of the interior of the cell difficult. Accordingly, the interior of the cell is polluted by the sample used previously; therefore, the exact value can not be obtained for the present sample. For cleaning the cell perfectly, the cell is necessary to be removed from the measuring optical path of the measuring instrument and reset to the original position for each of the measurements. It is extremely hard or impossible to effectively measure many samples one after another.

BRIEF DESCRIPTION OF THE INVENTION

A object of the present invention is to provide a cell for measurement is which the discharge of the sample and the cleaning of the cell are very easy even if the sample receiving portion is narrow and its volume is small. For this object, a injection tube for cleaning liquid is provided at the opening of the cell and a suction tube reaching to the bottom of the cell is also given. The construction of the cell like this makes the discharge of the sample, the injection and the discharge of the cleaning liquid easy.

Another object of the present invention is obtain a cell in which many measurements are continuously and effectively performed with only one cell. For this object the injection tube is connected to a pump which pumps out a predetermined constant volume of the cleaning liquid supplied to the cell, and the suction tube is connected with a suction pump through an electromagnetic valve for discharging the sample and the cleaning liquid completely. These operation are performed automatically using timers.

Another object of the present invention is to provide a cell attachment which can be attached to any conventional type of the cell for performing the measurement as described above. For this object, the attachment is comprised of a injection tube and a suction tube attached to a holder plate. When the holder plate is attached to a conventional cell, sample injection and cleaning are to be performed effectively.

Other objects and features of the present invention will be apparent from the following description.

DETAILED DESCRIPTION

Figure 3:
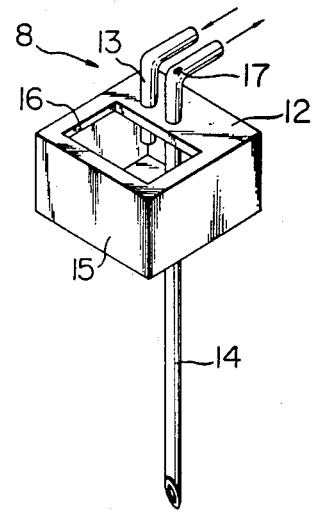
FIG. 3 is oblique views of parts of a disassembled cell.
Figure 3:
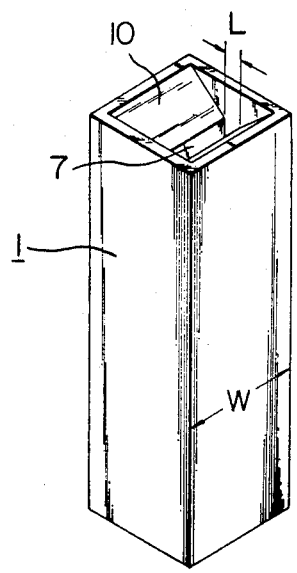

An embodiment according to the present invention will be described referring to FIGS. 3-5 hereafter.

The device according to the present invention comprises a cell (1) for receiving a sample (2), a attachment portion (8) attached so as to be freely set on and removed from the cell (1), and a cleaning device (9) connected to the attachment portion.

Figure 1:
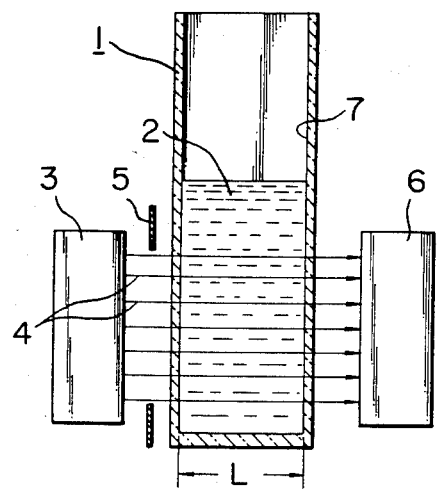
FIG. 1 is a sectional drawing of the standard cell.
Figure 2:
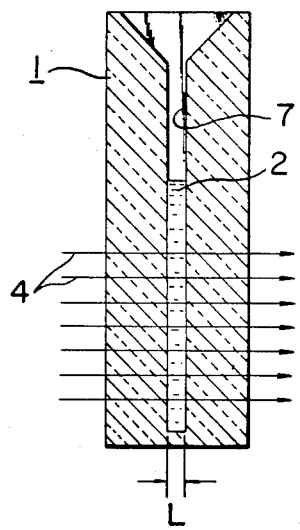
FIG. 2 is a sectional drawing of a cell having a narrowed sample receiving portion.

Said cell (1) is wholly composed of transparent glass, its shape being of a square prism having an opening (10) on the upper edge of the cell, and a bottom portion (11) at on the bottom. The shape and the size of the interior of the cell (1) depend upon the object of use and the kind of sample (2). The cell shown in FIG. 1 has the shape of a square prism with an optical pass length (L) of about 10 mm. The cell shown in FIG. 2 and FIG. 3 has a width (W) about the same as that of the cell shown in FIG. 1, but the sample receiving portion (7) is narrow with an optical length (L) of 2-0.5 mm. The upper portion of the cell has an opening (10) inclined with respect to the upper end of the cell. The shape of the cell is not limited to be prism like, but a cylindrical cell, triangular prism like cell and the others may be used.

Said attachment portion (8) comprises a holder plate (12) to be attached to the cell (1) so as to be freely set and removed. The holder plate (12) has a sample injection tube (13) and a suction tube (14) for a sample and cleaning liquid. When the holder plate (12) is coupled to the opening portion (10) of the cell (1), said plate forms a fixing guide (15) around the cell. The upper surface of the holder plate (12) has an opening (16) for injecting the sample (2). The injection opening (16) has a large enough dimension for putting in the sample from the tip of a pipette, a nozzle for partial injection, etc..

The shape of the holder plate (12) is not limited to that shown in the diagram. It can be varied according to the shape of the cell into cylindrical, triangular prismatic or other special ones.

The opening (10) of the cell may be freely designed so that it may not surround the whole periphery of the cell or it may partially surround the cell with a switchable stopper. The lower end of an injection tube (13) faces toward the opening portion (10). A suction tube (14) has enough length for its lower end to reach the bottom (11) of the cell (1). Its diameter is sized so that it can be inserted in the narrow sample receiving portion (7). The position where the suction tube is attached is determined so that it can be easily inserted into the sample receiving portion (7) and does not affect the passing position of the ray (4) as shown in FIG. 5. The lower end portion of the suction tube is preferably cut obliquely and the sharp tip is made to reach to the bottom (11). Accordingly, the sample and the cleaning liquid in the cell (1) can be completely sucked out. A small hole (17) for ventilation is drilled at the projected portion of the suction tube. This hole (17) prevents the sample liquid to be measured next from being sucked to flow out after discharging the cleaning liquid by suction because of surface tension, the loss of pressure reduction in the tube connected to the suction tube (14) etc..

Figure 5:
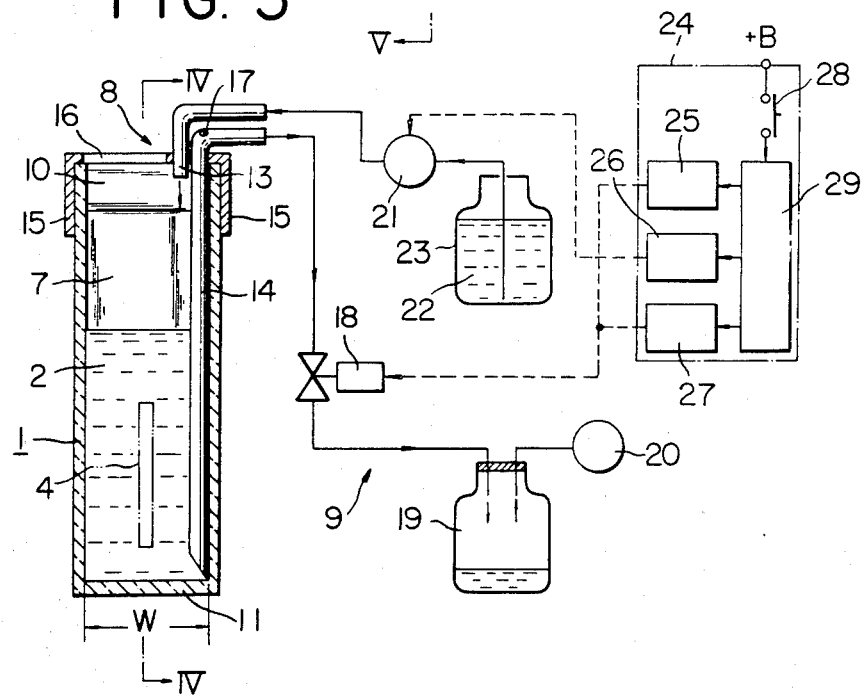
FIG. 5 is a cross sectional view along the V—V line of FIG. 4, and showing a cell according to the present invention with a diagram showing piping and wiring to a cleaning device for the cell.

A concrete example of the piping and wiring of said cleaning device is shown in FIG. 5 in which said suction tube (14) is tightly connected to a discharge bottle (19) through an electromagnetic valve (18). The discharge bottle (19) is tightly connected to a suction pump (20). Said injection tube (13) is connected to a bottle (23) for cleaning liquid filled with said liquid (22) through a constant volume pump (21).

Said electromagnetic valve (18), said suction pump (20) and said constant volume pump (21) are controlled by a timer circuit (24). The timer circuit comprises a first timer (25), a second timer (26) and a third timer (27). The first timer (25) and the third timer (27) are coupled with said electromagnetic valve (18) and the suction pump (20), and the second timer (26) is coupled with the constant volume pump. Turning on a switch (28) from electrical source (+B) operates said first timer (25), said second timer (26) and said third timer (27) sequentially through a control circuit (29). For example, these timers intermittently operate sequentially with respective intervals of 1 second, 1 second and 2 seconds for respectively discharging the sample, injecting the cleaning liquid and discharging the cleaning liquid automatically.

The operation of the device according to the present invention will be described in the following.

Figure 4:
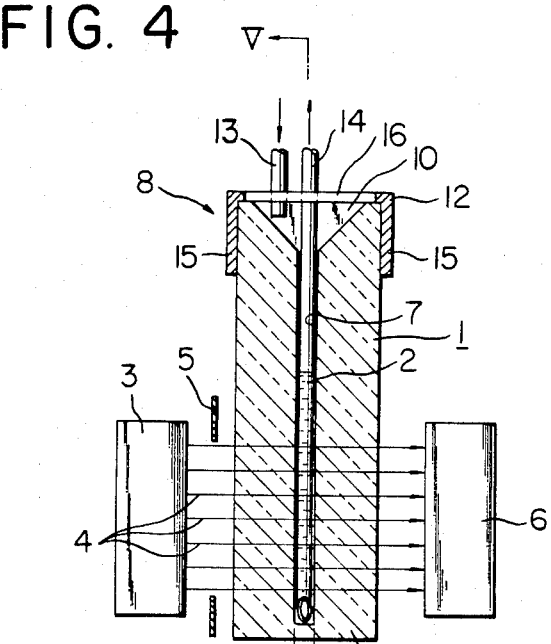
FIG. 4 is a cross sectional view along the IV—IV line of FIG. 5, and showing an assembled cell.

As shown in FIG. 4 the cell (1) is set in the optical path from a light source (3) to a detector (6) through a slit plate (5). The attachment portion (8) is coupled to the cell (1). In this state, the sample liquid (2) is put into the injection opening (16) with a pipette. A ray (4) with predetermined wave length is radiated for the optical measurement of such as absorbance.

After the measurement, if the switch (28) of the timer circuit (24) is turned on, the first timer signals for 1 sec to open the electromagnetic valve (18) so that the sample (2) which has been measured in the cell (11) is sucked out by the suction tube (14), being discharged to the bottle for discharged liquid (19). When the output of the first timer becomes null, the electromagnetic valve (18) is closed, the suction being stopped.

Next, a signal for one sec from the second timer (26) operates the constant volume pump (21) for supplying a predetermined volume of cleaning liquid (22) to the cell (1) through the injection tube (13) to fill the cell almost fully. When the output of the second timer (26) becomes zero the constant volume pump (21) ceases to operate.

The output having the duration of 2 sec from the third timer opens the electromagnetic valve (18) to suck up and discharge the cleaning liquid (22) in the cell (1).

In the first process, the sample which has been measured is perfectly sucked out, in the second process the cleaning liquid is injected into the cell (1) for cleaning the interior, and in the third process, the cleaning liquid is perfectly discharged to clean the cell (1) even if the sample receiving portion (7) is narrow.

Following the injection of the sample, the measurement is to be performed. After cleaning the cell for the previous sample, the injected new sample may be sucked little by little due to the surface tension of the sample or the pressure reduction loss in the tube connecting the cell and the suction pump. However, according to the present invention, the suction tube is provided with a small hole (17) as an escape of minimal pressure for preventing the sample from being sucked out.

Further, since the cleaning liquid in the cell can be discharged without leaving even a drop, the cleaning operation need not to be repeated. However, the cleaning operation may be repeated many a time, if desired, by controlling the second and third timers with the counter of the control circuit (29).

As described above, the cell according to the present invention demonstrates the ability of increasing the measurement accuracy because of the perfect discharge of the sample measured once and the cleaning liquid and the sufficient cleaning of the interior of the cell.

Once the cell is set fixedly on the cell fixing seat in the optical path of the optical measuring device, many measurements can be performed easily and continuously with a single cell, eliminating operations of setting and removing cells for one measurement apiece. Thus, the measuring operation is made more effective as compared with the conventional operation. Even a special type of cell can be used for the measurement by attaching a corresponding type of the attachment and the timer circuit allows the continuous and automatic sample measurement.

What is claimed is:

1. A cell for optical measurement, comprising a cell for receiving a sample, said cell being wholly composed of rigid transparent rigid material, said cell having an opening at its upper end, said cell having a sample receiving chamber communicating with said opening and with a narrow thickness in the range of 2-0.5 mm as an optical pass length, said sample receiving chamber having a width of over several times said thickness, an attachment portion attached to the cell and comprising a holder plate freely settably and removably attached at the opening of said cell, said holder plate having an injection tube whose lower end faces said cell opening for injecting thereinto a cleaning liquid, said holder plate having an elongate suction tube extending through said cell opening and with its lower end reaching to the bottom of the sample receiving chamber, said holder plate having an injection opening communicating with the cell opening for placing therein the sample, a cleaning device connected to said attachment portion and having a timer circuit, said cleaning device having a cleaning liquid input line including a constant volume pump connected from a cleaning liquid source to said injection tube for injecting therethrough cleaning liquid into said sample receiving chamber, said cleaning device having a suction line comprising a suction pump connected through an electromagnetic valve to said suction tube for removing sample and cleaning liquids from said sample receiving chamber, said timer circuit having a first timer and a third timer operatively associated with said suction line for timing withdrawal from said sample receiving chamber of a measured sample and cleaning liquid respectively, said timer circuit having a second timer operatively associated with said cleaning liquid input line for timing injection of cleaning liquid into said sample receiving chamber, and a control circuit for controlling said three timers.

2. A cell for optical measurement as claimed in claim 1, wherein said control circuit individually connects the second timer for injecting the cleaning liquid and to the third timer for discharging the cleaning liquid for operating alternately a plural number of times.

3. A cell for optical measurement as claimed in claim 1, in which said suction tube has a small hole therein between said cell opening and said suction line to prevent sucking liquid thereinto after disabling of said suction by said control circuit.

4. A cell for optical measurement as claimed in claim 3, wherein said first and third timers are operatively connected to said electromagnetic valve for turning same on and off.

5. A cell for optical measurement as claimed in claim 3, wherein said tubes have outside diameters approaching the thickness of said chamber.

6. A cell for optical measurement as claimed in claim 1, in which said cell chamber has sloped, upward divergent walls at its upper end, said holder plate having a top wall through which extend said tubes, said tubes being close adjacent with said injection tube opening downward onto one of said divergent walls, said suction tube passing downward between said divergent walls, said injection opening being beside said tubes and occupying a substantially larger portion of said top wall, said injection opening extending laterally over substantial portions of both divergent walls and said chamber, said tubes being adjacent one edge of said chamber and said injection opening being over the other edge and the central portion of said chamber, so as to allow room for insertion of a pipette containing liquid sample to be measured.

* * * * *